US00PP22292P3

(12) United States Plant Patent
Lowe

(10) Patent No.: US PP22,292 P3
(45) Date of Patent: Dec. 6, 2011

(54) KIWIFRUIT PLANT NAMED 'ZESY003'

(50) Latin Name: *Actinidia chinensis*
Varietal Denomination: ZESY003

(75) Inventor: Russell G. Lowe, Te Puke (NZ)

(73) Assignee: Zespri Group Limited, Mount Maunganui South (NZ)

( * ) Notice: Subject to any disclaimer, the term of this patent is extended or adjusted under 35 U.S.C. 154(b) by 0 days.

(21) Appl. No.: 12/660,393

(22) Filed: Feb. 24, 2010

(65) Prior Publication Data

US 2010/0333242 P1 Dec. 30, 2010

Related U.S. Application Data

(60) Provisional application No. 61/269,966, filed on Jun. 30, 2009.

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP11,066 P 9/1999 Lowe et al.

*Primary Examiner* — June Hwu
(74) *Attorney, Agent, or Firm* — Knobbe Martens Olson & Bear, LLP

(57) ABSTRACT

A new and distinct kiwifruit variety is disclosed. The variety results from selection among a population of seedlings derived from crossing the kiwifruit selections known as Kuimi 79-1-1 (not patented) and 30-03-05c.94 (not patented). The fruit of this new kiwifruit variety is characterized by moderate to large fruit size, high natural yield potential, ovoid shape, yellow flesh color, and potential for long storage. The new kiwifruit variety has been named 'ZESY003'.

5 Drawing Sheets

Latin name of the genus and species of the plant claimed: *Actinidia chinensis.*

Variety denomination: 'ZESY003'.

BACKGROUND AND SUMMARY OF THE INVENTION

The invention relates to the discovery and asexual propagation of a new and distinct variety of kiwifruit, *Actinidia chinensis* cv. 'ZESY003', as herein described and illustrated. The new kiwifruit variety 'ZESY003' was selected from a population of seedlings derived from crossing two kiwifruit selections Kuimi 79-1-1 (not patented) and 30-03-05c.94 (not patented) in the course of a planned kiwifruit variety breeding program. The cross was made in November 1995 at Te Puke, Bay of Plenty, New Zealand. The new variety was selected 51-17-29b.97 and has been named 'ZESY003'.

The new kiwifruit variety 'ZESY003' may be distinguished from presently available *Actinidia* cultivars by the following distinguishing characteristics:

The fruit of the new kiwifruit variety 'ZESY003' maintain their firmness in cold store and at room temperature for much longer than those of 'Hort16A' (U.S. Plant Pat. No. 11,066).

'ZESY003' produce larger fruit than those of 'Hort16A' and also produce more flowers.

The fruit shape at the stylar end of the new variety 'ZESY003' has a slight indentation surrounding a protrusion compared with that of 'Hort16A', which extends into a characteristic 'beak'.

The flesh of the new kiwifruit variety 'ZESY003' fruit is yellow in color (similar to 'Hort16A') when ripe for consumption, compared with 'Hayward', which is green in color.

'ZESY003' is tetraploid compared with 'Hort16A' which is diploid.

'ZESY003' is distinguished from its maternal parent (Kuimi 79-1-1) by characteristics including fruit shape, Kuimi 79-1-1 fruit are maliform, concave at the stalk attachment and slightly protruding at the stylar end with no stylar cavity; while fruit of 'ZESY003' are ovoid, almost flat at the stalk attachment and flat with an open cavity at the stylar end.

'ZESY003' is distinguished from its paternal parent (30-03-05c.94) as it is a female fruit kiwifruit variety whereas 30-03-05c.94 is a male non-fruit baring kiwifruit.

Asexual propagation of the new kiwifruit variety 'ZESY003', at Te Puke, Bay of Plenty, New Zealand, by grafting shows that the unique combination of characteristics of the variety come true to form and are established and transmitted through succeeding propagation. In order to obtain true-to-type clones of the initial plant, asexually propagated plants were obtained by grafting dormant buds from the original seedling onto rootstocks.

BRIEF DESCRIPTION OF THE DRAWINGS

The accompanying photographs show typical specimens in full color of the fruit, flowers, and leaves of the new variety 'ZESY003', plants observed were three years old. The colors as depicted are as nearly true as is reasonably possible in a color representation of this type.

DETAILED DESCRIPTION OF THE PREFERRED EMBODIMENT

The following is a detailed description of the new variety. The specimens described were grown at Te Puke, Bay of Plenty, New Zealand. The observations were made on vines grafted onto existing *A. deliciosa* seedling rootstock, and managed under standard orchard practice. This included growing the plants on a standard pergola structure at a height of 1.8 m, and each plant was allowed to occupy a canopy area of approximately 15 $m^2$. The plants were three years old when described, and considered mature. Random measurements of each characteristic were obtained from samples of 6 plants.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart 2001 edition published by The Royal Horticultural Society, London, England.

PLANT AND FOLIAGE

The plant is a female plant that is tetraploid and expresses a twining habit of medium vigor.

Tomentose hairs are present on the young shoot at low density. Anthocyanin (red) coloration of the growing tip is absent or very weak on most shoots.

The mature one-year-old shoots of the plant are smooth and colored orange-brown (R.H.S.165B) on the upper side. There are a many large lenticels (2.8 mm average diameter), which are yellow-white in color (R.H.S. 158B), and elliptical in shape. The leaf scar is moderate in size (similar to 'Hort16A'). Mature one-year-old shoots average 13.3 mm in diameter between bud 5 and 6.

Figure 7:
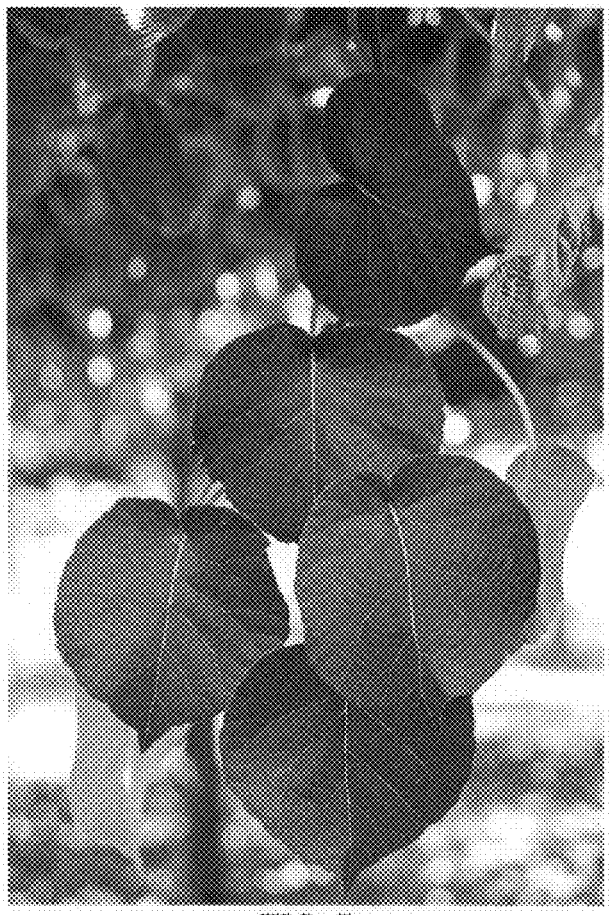
FIG. 7 shows mature leaves of the new kiwifruit variety 'ZESY003' (on the vine).
Figure 8:
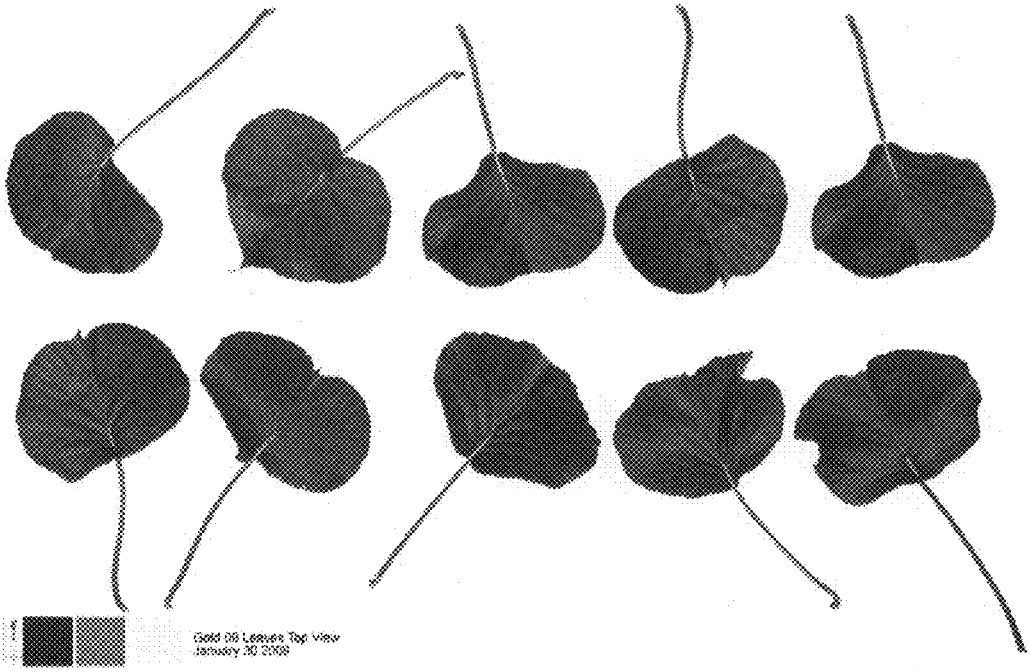
FIG. 8 shows mature leaves of the new kiwifruit variety 'ZESY003' from above (adaxial surface) (in the studio).
Figure 9:
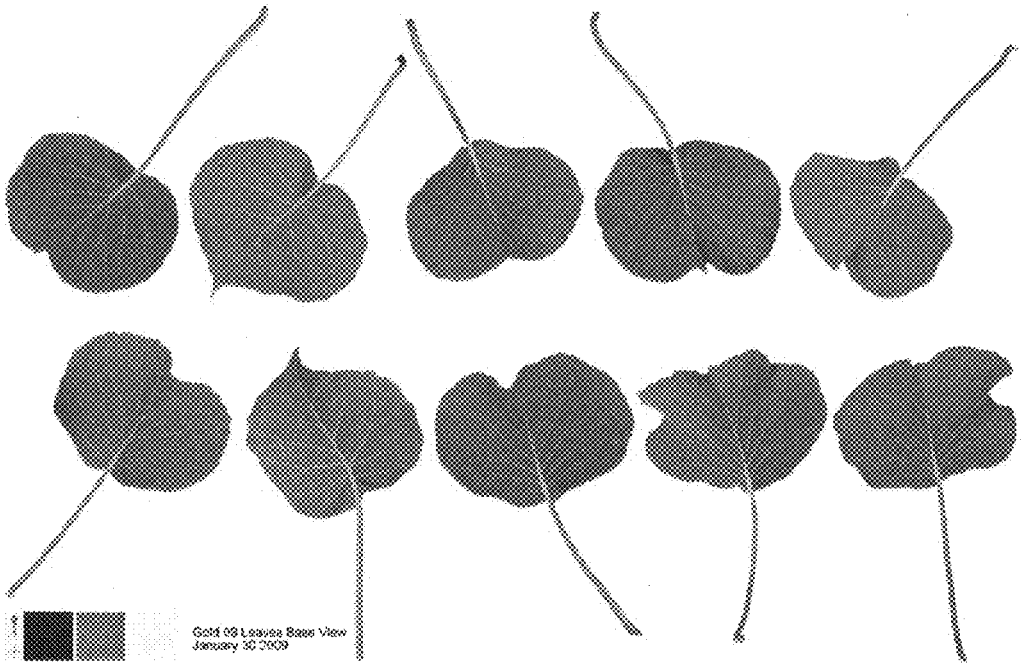
FIG. 9 shows mature leaves of the new kiwifruit variety 'ZESY003' from below (abaxial surface) (in the studio).

The leaf of 'ZESY003' is cordate in shape with an emarginated-with-cuspidate shaped leaf tip (FIG. 7, FIG. 8, FIG. 9) and average approximately 113 mm in length and 144 mm in width, the texture of a mature leaf is considered to be moderately rough. The leaf bases are open. The color of the leaf blade is deep green (R.H.S. 136A) on the upper surface and greenish-yellow (R.H.S.147B) on the lower surface, with no variegation observed. Leaf petioles are approximately 133 mm long and have strong anthocyanin coloration on the upper side of the petiole (R.H.S. 59A). Petioles have a sparse covering of very short, soft hairs that are not conspicuous without close inspection. On the underside of the leaf there are hairs on the sides of the veins, no spines have been observed.

INFLORESCENCE

The number of flowers in each inflorescence is typically between one to three flowers, with each inflorescence comprising a single king flower that produce the largest fruit and up to two side flowers (0.20 per inflorescence on average) that produce smaller fruit. Each fruiting one-year-old shoot typically develops between three and seven inflorescences, with an average of 5.3.

Flower pedicels average approximately 43 mm in length at mid-bloom.

Figure 6:
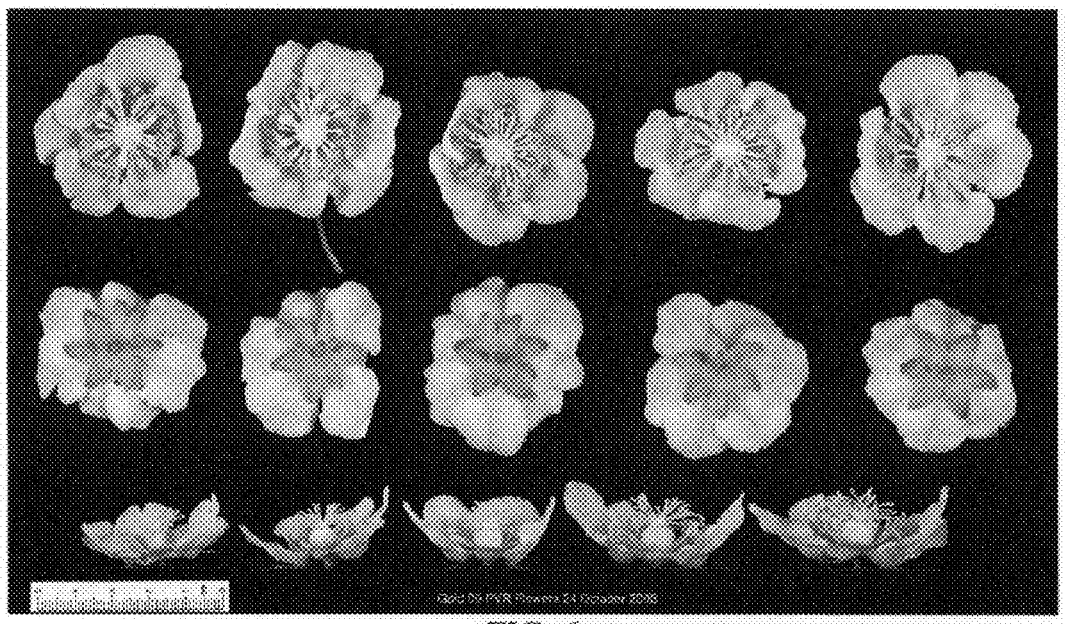
FIG. 6 shows the flowers of the new kiwifruit variety 'ZESY003' (in the studio).

There are between six and ten petals on each flower, with an average of 6.7. The petals are arranged overlapping and are white in color (R.H.S. 158B) when fully open, but with a light green base (R.H.S. 146C and 171C) (FIG. 6). Petals are involute in shape in cross-section and petals are moderately crimped. Flowers also contain between six and eight sepals (6.5 on average) that are mainly green in color (R.H.S. 154A), but with a yellow-brown color (R.H.S. 164C) around the edges and on parts of the sepals (FIG. 6). A 3 mm wide calyx ring is often present. Each flower produces between 30 and 39 styles (34 on average) with an erect attitude that are 8.2 mm long on average and white in color (R.H.S. 155D). There are an average of approximately 63 stamens per flower with yellow anthers (R.H.S. 15A).

Ovaries of the king flower are covered in fine hairs that are white in color (R.H.S. 155D). Anthocyanin (red) coloration of the ovaries in cross-section is absent at mid-bloom. Ovaries of the king flower have a mean length of 7.7 mm and are ovoid in shape.

FRUIT

Figure 3:
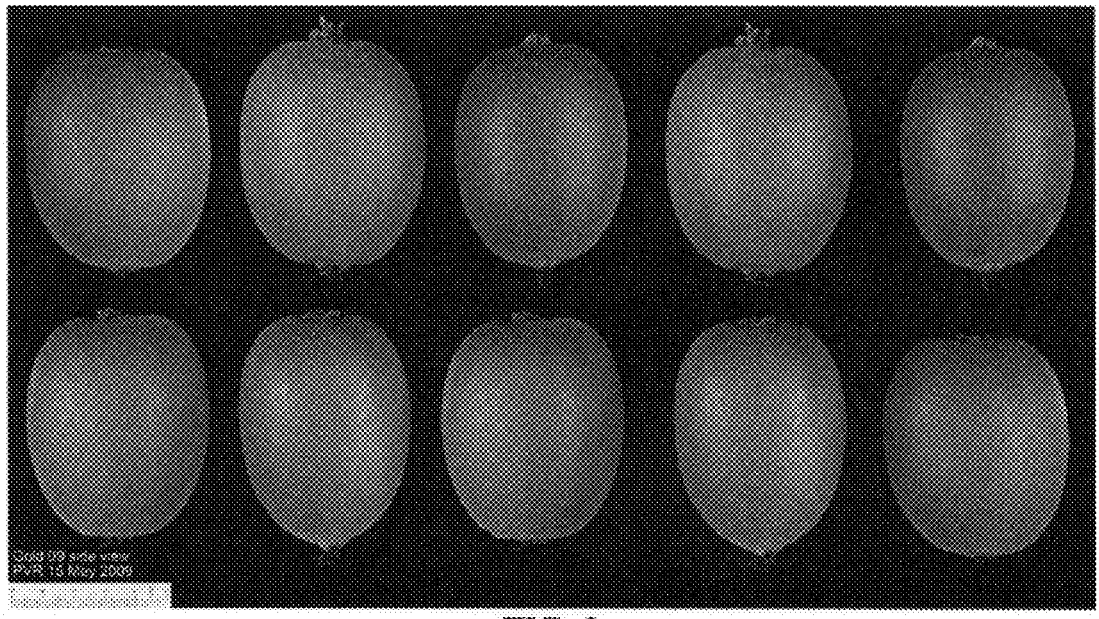
FIG. 3 shows typical fruit of the new kiwifruit variety 'ZESY003' (in the studio).
Figure 4:
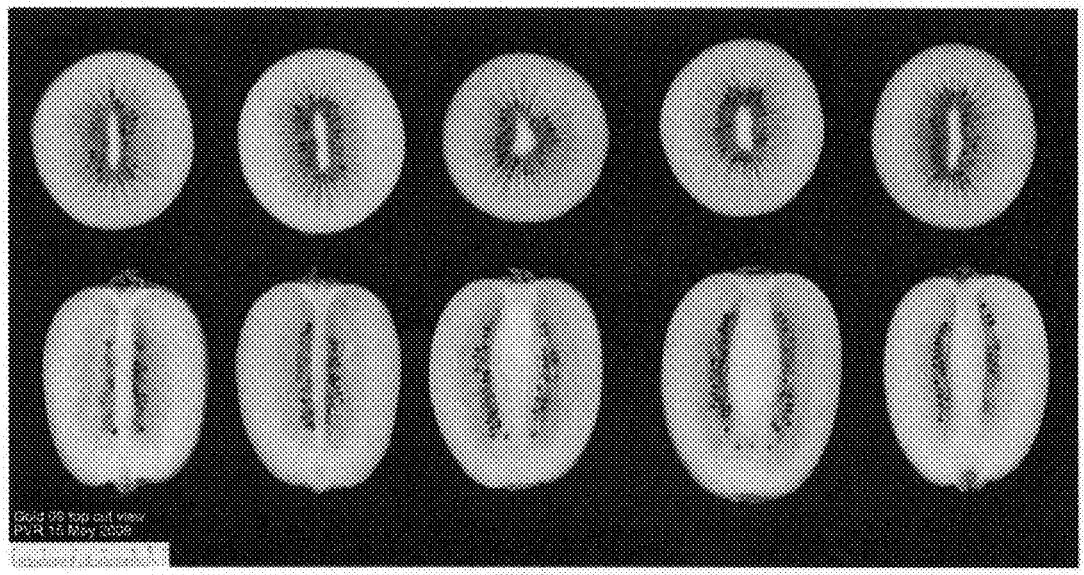
FIG. 4 shows the fruit of the new kiwifruit variety 'ZESY003' in longitudinal-section and cross-section (in the studio).

'ZESY003' fruit are moderate to large in size, approximately 118 g in weight on average when vines were thinned to approximately 60 fruit per square meter of female canopy. The fruit dimensions average 67.4 mm in length, 55.8 mm maximum width, and 51.6 mm minimum width. The general fruit shape in longitudinal section is ovoid, with the general shape of the stylar end being a slight dent surrounding a slight protrusion (FIG. 3, FIG. 4), while the stalk end of fruit are either rounded or square. In cross-section, the fruit shape at the median part of the fruit varies circular to partially elliptic, with most fruit being at least partially elliptic in shape (FIG. 4).

Fruit stalks are of medium length, averaging 56 mm long and 3.1 mm in diameter and are brown in color (R.H.S. 199C and 200C).

Soft brown (R.H.S. 165C) hairs are present on the mature fruit, but hairs are very short and occur at very low density. The skin of fruit varies between yellow-brown and green-brown in color (R.H.S. 199A and 148A) when fruit have been protected from direct sun exposure, but the skin changes to dark brown in color (R.H.S. 200D) on exposed fruit. The skin is covered with numerous lenticels that are light orange-brown in color (R.H.S. 164B) and are quite conspicuous. The combination of lenticels and underlying skin colors give the fruit an overall appearance of a light brown color (199B) when viewed from a distance of 30 cm or more.

The outer pericarp is initially a light green color (R.H.S. 164C) during early fruit development. The outer pericarp then gradually changes to a light yellow color (R.H.S. 10D) over a six to eight week period as fruit mature during March and April, reaching a yellow flesh hue angle of 103° by approximately April 19 in the Te Puke region of New Zealand. The inner pericarp is light yellow in color (R.H.S. 10C) at maturity for consumption (FIG. 4). The core of the mature fruit is yellowish-white (R.H.S. 11D), ellipsoid in shape, and is approximately 10.2 mm in average diameter. Each fruit contains between 29 and 37 locules (33 on overage) and between 28 and 40 seeds can be counted on a transverse slice made through the middle of the fruit (33 on average).

Fruit are very sweet and tangy with a mild lime flavor and smooth and juicy texture. Fruit can be ripened soon after they have been harvested in late March or early April in the Te Puke region of New Zealand using ethylene gas. Fruit remain firm above 1 kgf in coldstore for 24 to 30 weeks and will also maintain eating firmness for one to two weeks shelf life at 20° C. The fruit average 17.7% soluble solids (measured as °Brix) and contain 118 mg of vitamin C and 1.13 g of titratable acidity (g citric acid equivalents) per 100 g of fresh weight at maturity for consumption.

CULTIVATION

'ZESY003' plants can be grown on the same rootstocks as other standard varieties such as 'Hayward' and 'Hort16A'. Rootstocks currently being used in New Zealand include *A. deliciosa* seedlings, *A. chinenis* seedlings, and 'Kaimai' (not patented).

Figure 5:
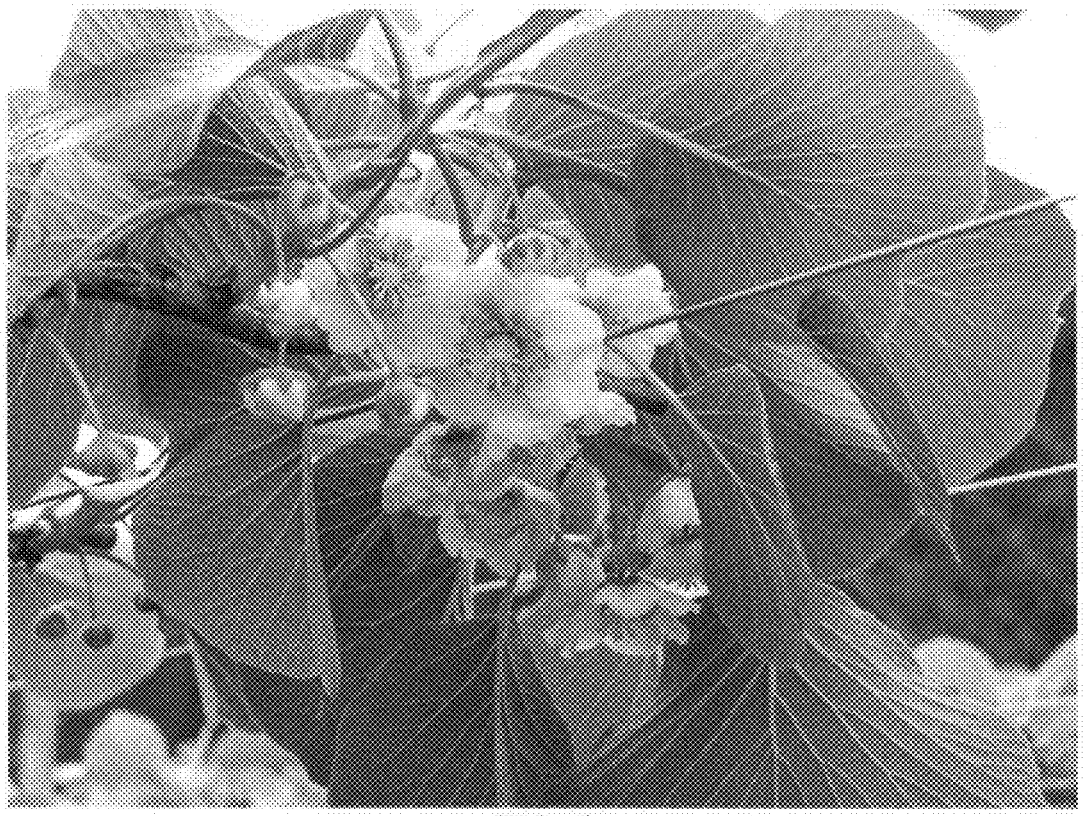
FIG. 5 shows the flowers of the new kiwifruit variety 'ZESY003' (on the vine).

Vegetative bud break occurs in late August in the Te Puke region of New Zealand, with flowering commencing in mid October, with a flowering period of approximately 14 days (FIG. 5). In the Te Puke region of New Zealand, approximately ⅔ of the dormant 'winter' buds burst in spring during budbreak and virtually 100% of these shoots will produce flowers. All flowers produced appear capable of setting a fruit that will survive to harvest, if they are pollinated. The fruit attain maturity for harvest according to the criteria of reaching 103° hue angle of the outer pericarp in late April in the Te Puke region of New Zealand. Leaves persist on the plants until early winter (June to July) in the Te Puke region of New Zealand.

Figure 1:
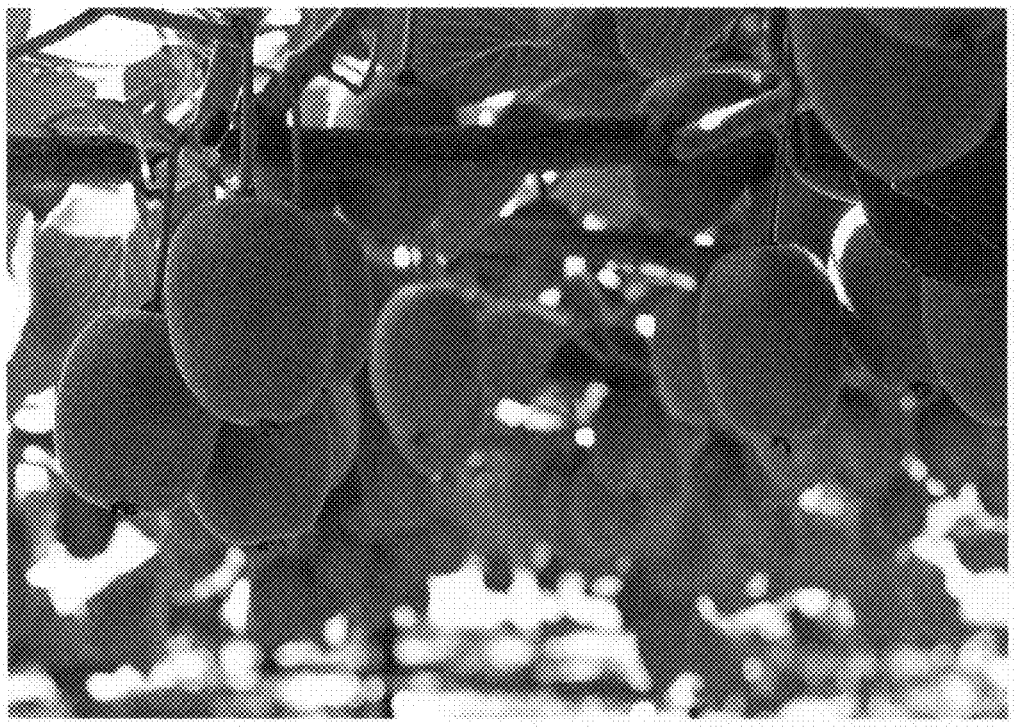
FIG. 1 shows typical fruit of the new kiwifruit variety 'ZESY003' (on the vine).
Figure 2:
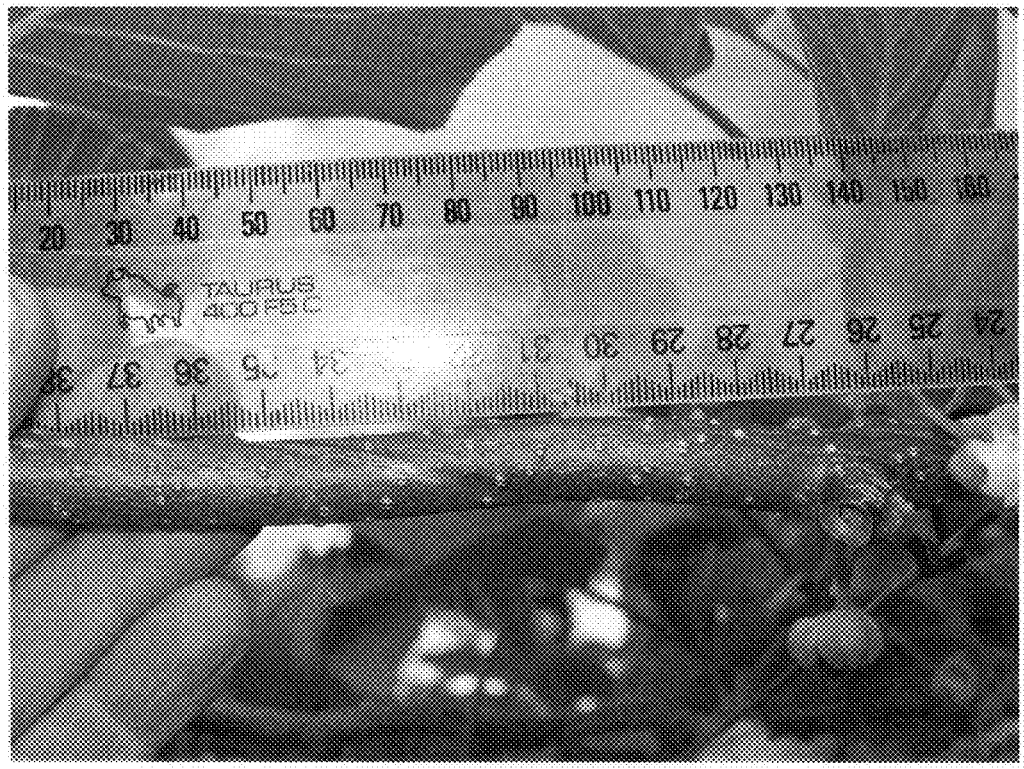
FIG. 2 shows typical one-year-old shoots (canes) of the new kiwifruit variety 'ZESY003' (on the vine).

In the absence of budbreak enhancing chemicals, plants produce high flower numbers with an average of 51 king flowers per meter of one-year-old cane in the Te Puke region of New Zealand. In non-thinned vines this would result in crop loads of 153 fruit per square meter of female canopy at standard cane spacings (FIG. 1). Fruit size is moderate to large (118 g) when thinned to a crop load of approximately 60 fruit per square meter of female canopy, but the high flower numbers of 'ZESY003' mean that it has the potential to consistently deliver high natural yields relative to other cultivars of kiwifruit currently being grown.

Dormant canes of 'ZESY003' appear to be susceptible to Latania scale (*Hemiberlesia lataniae*) and leaves appear to be susceptible to brown headed leafroller (*Ctenopseustis obliquana*). There is no evidence to suggest that fruitlets may be susceptible to *Sclerotinia sclerotiorum* infection, similar to 'Hort16A'. No other host susceptibility testing has been completed at this stage.

Observations to date suggest that 'ZESY003' plants has a similar plant hardiness zone to 'Hort16A' plants.

In post harvest storage, softening of harvested 'ZESY003' fruit can be delayed by placing fruit into cold storage. In this case, fruit can be successfully stored for between 24 and 30 weeks while maintaining average flesh firmness greater than one kgf. If fruit are removed from long term cold store at close to eating firmness, and returned to ambient temperatures, fruit can be held at 20° C. for one to two weeks for consumption.

We claim:

1. A new and distinct kiwifruit plant substantially as herein described and illustrated, characterized by fruit with a moderate-large fruit size, high natural yield potential, ovoid shape, yellow flesh color, and potential for long storage.

* * * * *